US00PP12163P2

(12) United States Plant Patent
Glicenstein

(10) Patent No.: US PP12,163 P2
(45) Date of Patent: Oct. 23, 2001

(54) CARNATION PLANT NAMED 'YODER DREAM'

(75) Inventor: Leon Glicenstein, Lebanon, IN (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/748,493

(22) Filed: Dec. 27, 2000

(51) Int. Cl.[7] ..... A01H 5/00
(52) U.S. Cl. ..... Plt./281
(58) Field of Search ..... Plt./281

(56) References Cited

U.S. PATENT DOCUMENTS

P.P. 5,787 8/1986 Barberet ..... Plt./281

*Primary Examiner*—Bruce R. Campell
*Assistant Examiner*—Kent L. Bell
(74) *Attorney, Agent, or Firm*—C. A. Whealy

(57) ABSTRACT

A distinct cultivar of Carnation plant named 'Yoder Dream', characterized by its large and full pink-colored flowers; early flowering habit; fragrant flowers; strong calyxes which resist splitting; good postproduction longevity with flowers maintaining good substance and color for more than two weeks in an interior environment; and resistance to *Fusarium oxysporum*.

2 Drawing Sheets

BACKGROUND OF THE INVENTION

The present invention relates to a new and distinct cultivar of Carnation plant, botanically known as *Dianthus caryophyllus* and hereinafter referred to by the name 'Yoder Dream'.

The new Carnation is a product of a planned breeding program conducted by the Inventor in Salinas, Calif. The objective of the breeding program is to create new cut Carnation cultivars having long flowering stems, early flowering, attractive flower color, and good flower form and substance.

Tne new Carnation originated from a cross made by the Inventor in 1994, in Salinas, Calif., of a proprietary Carnation seedling selection identified as code number 0140, as the male, or pollen, parent with the Carnation cultivar 'Nelson', not patented, as the female, or seed, parent.

The cultivar 'Yoder Dream' was discovered and selected by the Inventor as a flowering plant within the progeny of the stated cross in a controlled environment in Suba, Cundinamarca, Colombia, in October, 1995. The selection of this plant was based on its flower color and good flower form and substance.

Asexual reproduction of the new Carnation by terminal cuttings taken in a controlled environment in Suba, Cundinamarca, Colombia, has shown that the unique features of this new Carnation are stable and reproduced true to type in successive generations.

SUMMARY OF THE INVENTION

The cultivar 'Yoder Dream' has not been observed under all possible environmental conditions. The phenotype may vary somewhat with variations in environment such as temperature, daylength, light intensity, and water and nutritional status without, however, any variance in genotype.

The following traits have been repeatedly observed and are determined to be the unique characteristics of 'Yoder Dream'. These characteristics in combination distinguish 'Yoder Dream' as a new and distinct cultivar:

1. Large and full pink-colored flowers.
2. Early flowering.
3. Fragrant flowers.
4. Strong calyxes which resist splitting.
5. Good postproduction longevity with flowers maintaining good substance and color for more than two weeks in an interior environment.
6. Resistance to *Fusarium oxysporum*.

Plants of the new Carnation differ primarily from plants of the parent plants in flower form and substance.

Plants of the new Carnation can be compared to plants of the cultivar 'Barlo II Nora', not patented. In side-by-side comparisons conducted in Suba, Cundinamarca, Colombia, plants of the new Carnation and the cultivar 'Barlo II Nora' differ in the following characteristics:

1. Plants of the new Carnation have longer, stronger and thicker flowering stems than plants of the cultivar 'Barlo II Nora'.
2. Flowers of plants of the new Carnation are larger than flowers of plants of the cultivar 'Barlo II Nora'.
3. Calyxes of plants of the new Carnation very rarely split, whereas calyxes of plants of the cultivar 'Barlo II Nora' are prone to splitting.
4. Flowers of plants of the new Carnation are slightly less fragrant than flowers of plants of the cultivar 'Barlo II Nora'.

BRIEF DESCRIPTION OF THE PHOTOGRAPHS

The accompanying colored photographs illustrate the overall appearance of the new Carnation, showing the colors as true as it is reasonably possible to obtain in colored reproductions of this type. Colors in the photographs may differ slightly from the color values cited in the detailed botanical description which accurately describe the colors of the new Carnation.

The photograph on the first sheet comprises a side perspective view of a typical flowering stem of 'Yoder Dream' grown as a standard-type cut Carnation.

The photograph at the top of the second sheet comprises a close-up view of a typical flower of 'Yoder Dream'.

The photograph at the bottom of the second sheet comprises a close-up view of typical flowers of 'Yoder Dream' (left) and 'Barlo II Nora' (right).

DETAILED BOTANICAL DESCRIPTION

In the following description, color references are made to The Royal Horticultural Society Colour Chart except where general terms of ordinary dictionary significance are used. The following observations and measurements describe plants grown in Madrid, Cundinamarca, Colombia, under conditions which approximate commercial practice in a single-layer polyethylene-covered greenhouse. Four-week old rooted cuttings were planted in ground beds and pinched about 3 to 4 weeks later. During the production time, the following environmental conditions were measured: day temperatures, 19 to 24° C.; night temperatures, 4 to 12° C.; and light levels, about 3,000 to 5,000 foot-candles. Measurements and numerical values represent averages for six to ten typical flowering stems that were harvested from plants that were about 24 to 26 weeks after planting.

Botanical classification: *Dianthus caryophyllus* cultivar 'Yoder Dream'.

Commercial classification: Standard (disbudded)-type cut Carnation.

Parentage:

*Male or pollen parent.*—Proprietary *Dianthus caryophyllus* seedling selection identified as code number 0140, not patented.

*Female or seed parent.*—*Dianthus caryophyllus* cultivar 'Nelson' not patented.

Propagation:

*Type.*—Terminal tip cuttings.

*Time from sticking unrooted cuttings to planting.*—About 4 weeks.

*Root description.*—Fine, freely-branching.

Plant description:

*Flowering stem description.*—Aspect: Erect. Strength: Very strong, flexible. Length: About 86.4 cm. Diameter: About 3.75 mm. Internode length, between $4^{th}$ and $5^{th}$ node: About 9.5 cm. Texture: Smooth. Color: 147A, overlain with waxy bloom, close to 188A.

*Foliage description.*—Arrangement: Opposite; sessile. Aspect: Concave; reflexed. Length: About 14.75 cm. Width: About 9.2 mm. Shape: Linear. Apex: Sharply acute. Margin: Entire. Texture: Tough, leathery, waxy. Color: Young foliage, upper and lower surfaces: Darker than 147A, with waxy bloom, close to 188A. Mature foliage, upper and lower surfaces: Darker than 147A, overlain with waxy bloom, close to 188A.

Flowering description:

*Appearance.*—Single flowers grown as a standard (disbud); one flower per flowering stem.

*Flowering season response.*—Year-round under greenhouse conditions; plants flower about 24 to 27 weeks after planting rooted cuttings.

*Postproduction longevity.*—In an interior environment, flowering stems will maintain good color and substance for more than two weeks. Flowers persistent.

*Fragrance.*—Moderately fragrant; spicy, clove-like.

*Flower size.*—Diameter: About 9.5 cm. Depth (height): About 4.3 cm.

*Flower buds* (*at stage of showing color*).—Length: About 3.5 cm. Diameter: About 1.5 cm. Shape: Oblong. Color: Close to 54D.

*Petals/petaloids.*—Quantity: About 64, imbricate. Length: About 6.5 cm. Width: About 4.3 cm. Shape: Roughly spatulate. Apex: Rounded. Base: Attenuate to acute. Margin: Finely serrated giving a fringed appearance. Texture: Velvety, smooth, glabrous. Color: When opening, upper and lower surfaces: 54D to 55C; iridescent. Fully opened, upper and lower surfaces: 55C to 55D; iridescent.

*Sepals.*—Quantity: About 5 or 6, fused. Length: About 3.3 cm. Width: About 1.3 cm. Calyx diameter: Apex: About 2.5 cm. Base: About 1.7 cm. Shape: Roughly ovate. Apex: Acute. Texture: Tough, leathery; smooth; waxy, longitudinally ridged. Resistance to splitting: Very good, calyxes vary rarely split. Color: Upper surface: Close to 157A to white. Lower surface: Close to 146A.

*Reproductive organs.*—Androecium: Stamen number: Usually 2 or 3, most are transformed into petaloids. Stamen length: About 2.3 cm. Stamen color: White, close to 155D. Anther size: About 2 mm by 1 mm. Anther shape: Oblong. Anther color: White, close to 155D. Pollen: None observed. Gynoecium: Pistil quantity: Three, fused. Pistil length: About 3 cm. Pistil color: White, close to 155D. Receptacle size: About 1.1 cm by 8 mm. Receptacle color: Close to 151A.

*Seed.*—Seed production has not been observed.

Disease resistance: Plants of the new Carnation planted in soils heavily infested with *Fusarium oxysporum* have been observed to be highly resistant to *Fusarium oxysporum.*

It is claimed:

1. A new and distinct cultivar of Carnation plant named 'Yoder Dream', as illustrated and described.

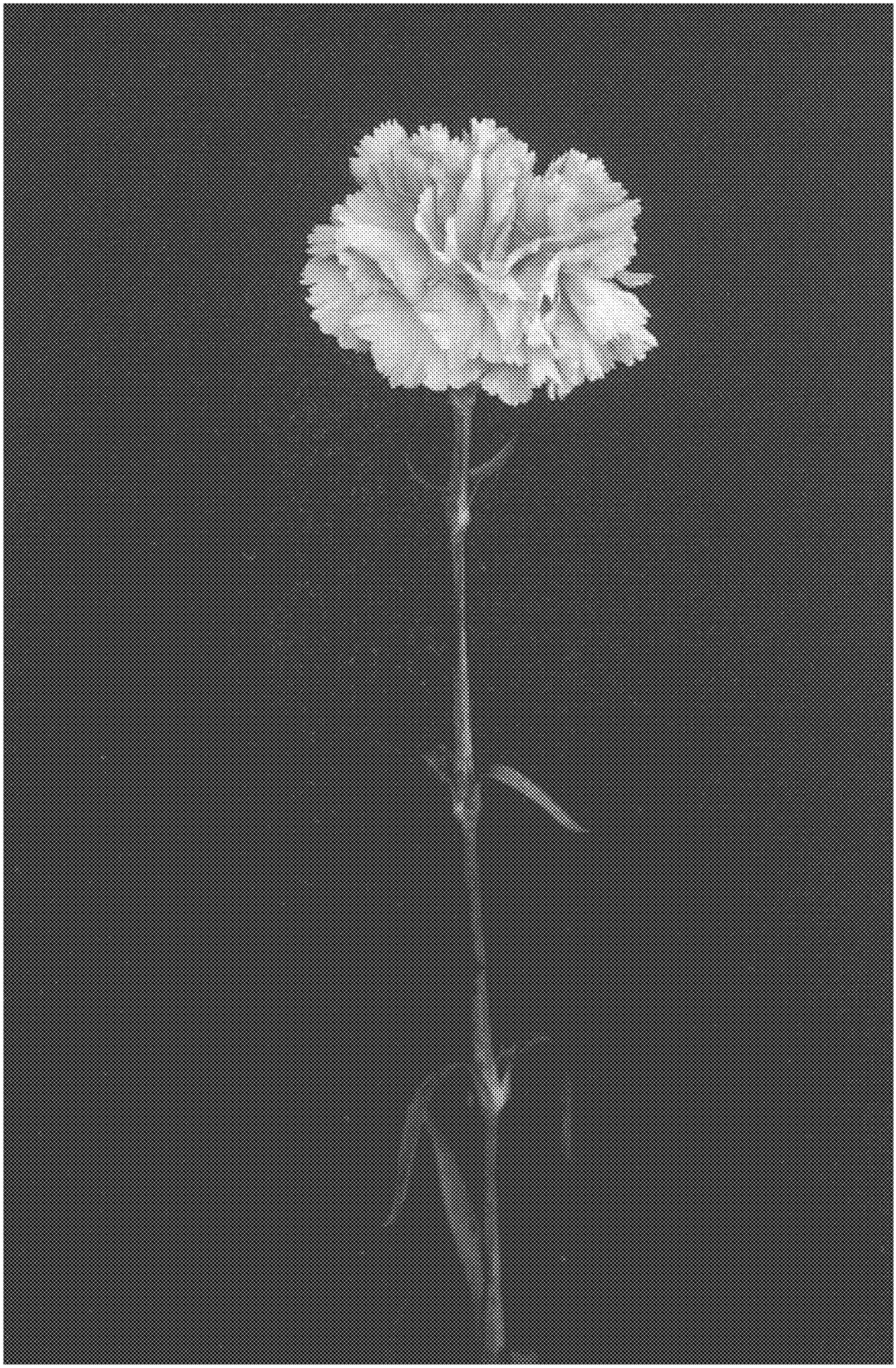

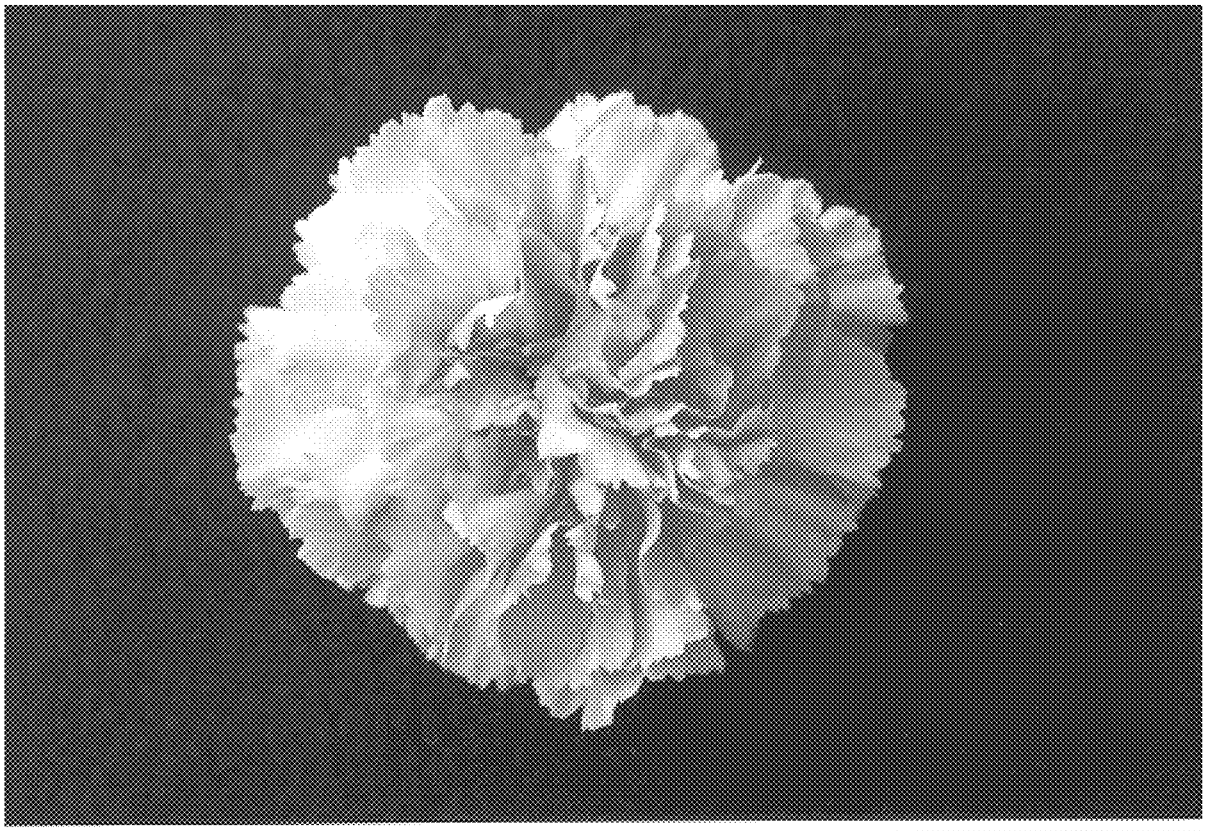
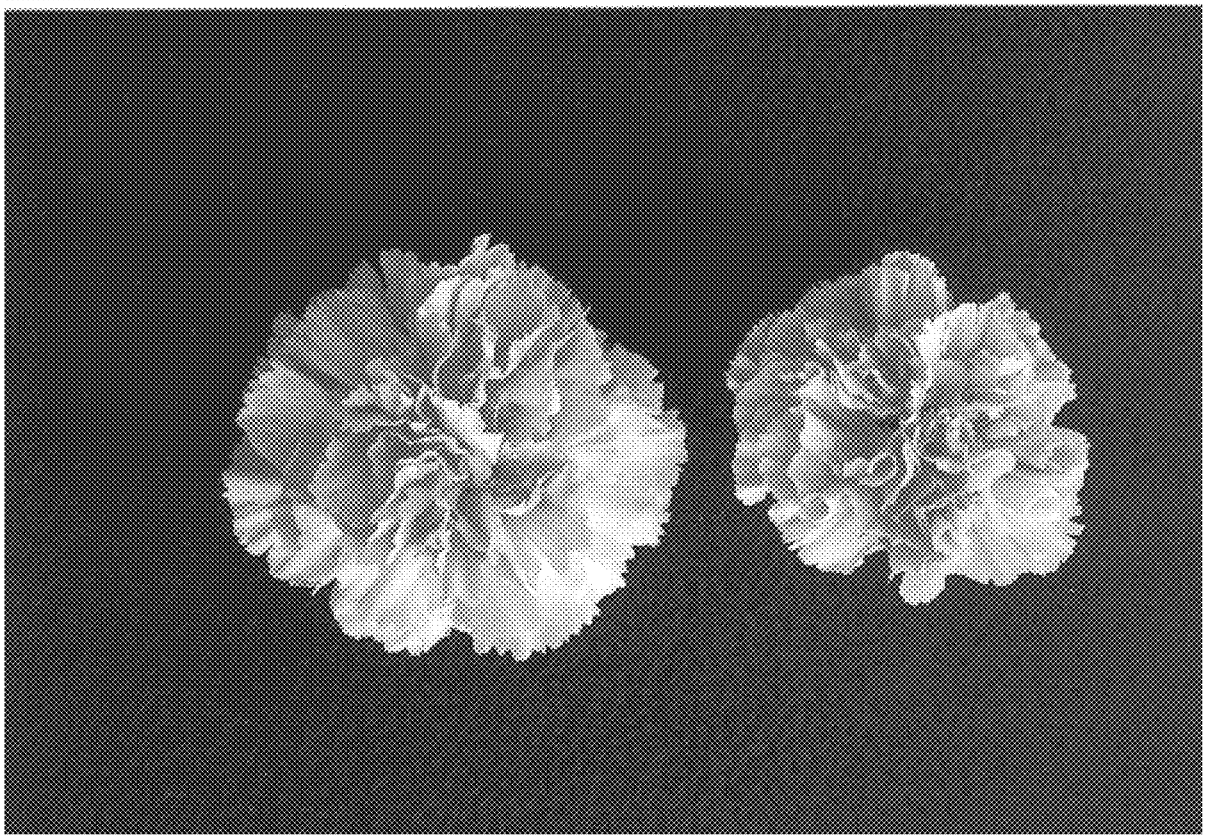

* * * * *